United States Patent
Suzuki et al.

[11] Patent Number: 5,912,333
[45] Date of Patent: Jun. 15, 1999

[54] DNA ENCODING CARBONIC ANHYDRASE

[75] Inventors: Shoichi Suzuki, Iwata-gun, Japan; James Nigel Burnell, Townsville, Australia

[73] Assignee: Japan Tobacco Inc., Tokyo, Japan

[21] Appl. No.: 08/492,027

[22] PCT Filed: Oct. 27, 1994

[86] PCT No.: PCT/JP94/01814

§ 371 Date: Aug. 15, 1995

§ 102(e) Date: Aug. 15, 1995

[87] PCT Pub. No.: WO95/11979

PCT Pub. Date: May 4, 1995

[30] Foreign Application Priority Data

Oct. 29, 1993 [JP] Japan .................................. 5/294278

[51] Int. Cl.$^6$ .................................................. C07H 21/04
[52] U.S. Cl. .................... 536/23.2; 536/23.1; 536/23.6; 435/232; 435/252.3; 435/252.33; 435/410; 435/320.1
[58] Field of Search ................. 536/23.2, 23.6; 435/232

[56] References Cited

FOREIGN PATENT DOCUMENTS

WO94/00977  1/1994  WIPO.

OTHER PUBLICATIONS

Hudspeth et al, Plant Physiol., vol. 98, pp. 458–464 (1992).
Burnell et al, Plant Physiol., vol. 92, pp. 37–40 (1990).
Fawcett et al, The Journal of Biological Chemistry, vol. 265, No. 10, pp. 5414–5417 (1990).
Roeske et al, Nucleic Acids Research, vol. 18, No. 11, p. 3413 (1990).
Majeau et al, Plant Physiol., vol. 95, pp. 264–268 (1991).
Raines et al, Plant Molecular Biology, vol. 20, pp. 1143–1148 (1992).
Keith et al, Plant Physiol., vol. 101, pp. 329–332 (1993).
Majeau et al, Plant Physiol., vol. 100, pp. 1077–1078 (1992).
Kogami et al, Transgenic Research, vol. 3, pp. 287–296 (1994).
Hayashi et al, Derwent WPI, Abstract: EP 504869.
Derwent WPI, Abstract: JP 04222527.
Creighton, T. E. "Proteins: Structure and Molecular Properties" Second Edition, W. H. Freeman and Company, New York, pp. 108, 109, 132, and 133, 1993.
Burnell et al. "Light Induction and the Effect of Nitrogen Status upon the Activity of Carbonic Anhydrase . . . " Plant Physiol. 94, 384–387, May 1990.
Sugiharto et al. "Glutamine Induces the N–Dependent Accumulation of mRNA Encoding . . . " Plant Physiol. 100, 2066–2070, Jan. 1992.
Relevant parts of the results of sequence search for Seq ID No's 2, 7, and 9, Feb. 1997.
Izui et al, Plant Cell Technology, vol. 5, No. 2, pp. 74–82 (1993).
di Guan et al., *Gene*, vol. 67, pp. 21–30 (1988).
Amann et al., *Gene*, vol. 40, pp. 183–190 (1985).
Hoffman et al., *Nucleic Acids Research*, vol. 19, No. 22, pp. 6337–6338 (1991).
Smith et al., *Gene*, vol. 67, pp. 31–40 (1988).
Bujard et al., *Methods in Enzymology*, [26] *A T5 Promoter–Based Transcription–Translation System for the Analysis of Proteins in Vitro and in Vivo*, vol. 155 (1987).
Studier et al., *Methods in Enzymology*, vol. 185, pp. 60–89 (1990).

*Primary Examiner*—Robert A. Wax
*Assistant Examiner*—Nashaat T. Nashed
*Attorney, Agent, or Firm*—Birch, Stewart, Kolasch & Birch, LLP

[57] ABSTRACT

A cloned DNA encoding carbonic anhydrase of a monocotyledon is disclosed.

8 Claims, No Drawings

SEQUENCE LISTING (1) GENERAL INFORMATION:

(iii) NUMBER OF SEQUENCES: 9

(2) INFORMATION FOR SEQ ID NO:1:

(i) SEQUENCE CHARACTERISTICS:
       (A) LENGTH: 651 amino acids
       (B) TYPE: amino acid
       (D) TOPOLOGY: linear (ii) MOLECULE TYPE: protein (xi) SEQUENCE DESCRIPTION: SEQ ID NO:1:

```
Tyr Thr Leu Pro Val Arg Thr Thr Thr Ser Ser Ile Val Pro Ala Cys
 1               5                  10                  15

His Pro Arg Ala Val Leu Leu Leu Arg Leu Arg Pro Pro Gly Ser Gly
                20                  25                  30

Ser Ser Gly Thr Pro Arg Leu Arg Arg Pro Ala Thr Val Val Gly Met
            35                  40                  45

Asp Pro Thr Val Glu Arg Leu Lys Ser Gly Phe Gln Lys Phe Lys Thr
    50                  55                  60

Glu Val Tyr Asp Lys Lys Pro Glu Leu Phe Glu Pro Leu Lys Ser Gly
65                  70                  75                  80

Gln Ser Pro Arg Tyr Met Val Phe Ala Cys Ser Asp Ser Arg Val Cys
                85                  90                  95

Pro Ser Val Thr Leu Gly Leu Gln Pro Gly Glu Ala Phe Thr Val Arg
            100                 105                 110

Asn Ile Ala Ser Met Val Pro Pro Tyr Asp Lys Ile Lys Tyr Ala Gly
        115                 120                 125
```

Thr Gly Ser Ala Ile Glu Tyr Ala Val Cys Ala Leu Lys Val Gln Val
    130                 135                 140

Ile Val Val Ile Gly His Ser Cys Cys Gly Gly Ile Arg Ala Leu Leu
145                 150                 155                 160

Ser Leu Lys Asp Gly Ala Pro Asp Asn Phe Thr Phe Val Glu Asp Trp
            165                 170                 175

Val Arg Ile Gly Ser Pro Ala Lys Asn Lys Val Lys Lys Glu His Ala
            180                 185                 190

Ser Val Pro Phe Asp Asp Gln Cys Ser Ile Leu Glu Lys Glu Ala Val
        195                 200                 205

Asn Val Ser Leu Gln Asn Leu Lys Ser Tyr Pro Phe Val Lys Glu Gly
        210                 215                 220

Leu Ala Gly Gly Thr Leu Lys Leu Val Gly Ala His Tyr Ser Phe Val
225                 230                 235                 240

Lys Gly Gln Phe Val Thr Trp Glu Pro Gln Asp Ala Ile Glu Arg
            245                 250                 255

Leu Thr Ser Gly Phe Gln Gln Phe Lys Val Asn Val Tyr Asp Lys Lys
            260                 265                 270

Pro Glu Leu Phe Gly Pro Leu Lys Ser Gly Gln Ala Pro Lys Tyr Met
        275                 280                 285

Val Phe Ala Cys Ser Asp Ser Arg Val Cys Pro Ser Val Thr Leu Gly
        290                 295                 300

Leu Gln Pro Ala Lys Ala Phe Thr Val Arg Asn Ile Ala Ala Met Val
305                 310                 315                 320

Pro Gly Tyr Asp Lys Thr Lys Tyr Thr Gly Ile Gly Ser Ala Ile Glu
            325                 330                 335

Tyr Ala Val Cys Ala Leu Lys Val Glu Val Leu Val Val Ile Gly His
            340                 345                 350

Ser Cys Cys Gly Gly Ile Arg Ala Leu Leu Ser Leu Lys Asp Gly Ala
        355                 360                 365

Pro Asp Asn Phe His Phe Val Glu Asp Trp Val Arg Ile Gly Ser Pro
        370                 375                 380

Ala Lys Asn Lys Val Lys Lys Glu His Ala Ser Val Pro Phe Asp Asp
385                 390                 395                 400

Gln Cys Ser Ile Leu Glu Lys Glu Ala Val Asn Val Ser Leu Gln Asn
            405                 410                 415

Leu Lys Ser Tyr Pro Leu Val Lys Glu Gly Leu Ala Gly Gly Thr Ser
            420                 425                 430

Ser Gly Trp Pro His Tyr Asp Phe Val Lys Gly Gln Phe Val Thr Trp
        435                 440                 445

Glu Pro Pro Gln Asp Ala Ile Glu Arg Leu Thr Ser Gly Phe Gln Gln
        450                 455                 460

Phe Lys Val Asn Val Tyr Asp Lys Lys Pro Glu Leu Phe Gly Pro Leu
465                 470                 475                 480

Lys Ser Gly Gln Ala Pro Lys Tyr Met Val Phe Ala Cys Ser Asp Ser
            485                 490                 495

Arg Val Cys Pro Ser Val Thr Leu Pro Ala Ala Gly Glu Ala Phe Thr
            500                 505                 510

Val Arg Asn Ile Ala Ala Met Val Gln Gly Tyr Asp Lys Thr Lys Tyr
        515                 520                 525

Thr Gly Ile Gly Ser Ala Ile Glu Tyr Ala Val Cys Ala Leu Lys Val
        530                 535                 540

Glu Val Leu Val Val Ile Gly His Ser Cys Cys Gly Gly Ile Arg Ala

```
545                 550                 555                 560
Leu Leu Ser Leu Gln Asp Gly Ala Pro Asp Thr Phe His Phe Val Glu
            565                 570                 575

Asp Trp Val Lys Ile Ala Phe Ile Ala Lys Met Lys Val Lys Lys Glu
            580                 585                 590

His Ala Ser Val Pro Phe Asp Asp Gln Trp Ser Ile Leu Glu Lys Glu
            595                 600                 605

Ala Val Asn Val Ser Leu Glu Asn Leu Lys Thr Tyr Pro Phe Val Lys
            610                 615                 620

Glu Gly Leu Ala Asn Gly Thr Leu Lys Leu Ile Gly Ala His Tyr Asp
625                 630                 635                 640

Phe Val Ser Gly Glu Phe Leu Thr Trp Lys Lys
            645                 650

(2) INFORMATION FOR SEQ ID NO:2:

(i) SEQUENCE CHARACTERISTICS:
        (A) LENGTH: 2178 base pairs
        (B) TYPE: nucleic acid
        (C) STRANDEDNESS: single
        (D) TOPOLOGY: linear (ii) MOLECULE TYPE: cDNA to mRNA (ix) FEATURE:
        (A) NAME/KEY: CDS
        (B) LOCATION: 1..1953

(xi) SEQUENCE DESCRIPTION: SEQ ID NO:2:

TAC ACA TTG CCC GTC CGT ACC ACC ACA TCC AGC ATC GTG CCA GCC TGC       48
Tyr Thr Leu Pro Val Arg Thr Thr Thr Ser Ser Ile Val Pro Ala Cys
 1               5                   10                  15

CAC CCC CGC GCC GTC CTC CTC CTC CGG CTC CGG CCC CCA GGC TCA GGC       96
His Pro Arg Ala Val Leu Leu Leu Arg Leu Arg Pro Pro Gly Ser Gly
                20                  25                  30

TCA TCC GGA ACG CCC CGT CTT CGC CGC CCC GCC ACC GTC GTG GGC ATG      144
Ser Ser Gly Thr Pro Arg Leu Arg Arg Pro Ala Thr Val Val Gly Met
            35                  40                  45

GAC CCC ACC GTC GAG CGC TTG AAG AGC GGG TTC CAG AAG TTC AAG ACC      192
Asp Pro Thr Val Glu Arg Leu Lys Ser Gly Phe Gln Lys Phe Lys Thr
50                  55                  60

GAG GTC TAT GAC AAG AAG CCG GAG CTG TTC GAG CCT CTC AAG TCC GGC      240
Glu Val Tyr Asp Lys Lys Pro Glu Leu Phe Glu Pro Leu Lys Ser Gly
65                  70                  75                  80

CAG AGC CCC AGG TAC ATG GTG TTC GCC TGC TCC GAC TCC CGC GTG TGC      288
Gln Ser Pro Arg Tyr Met Val Phe Ala Cys Ser Asp Ser Arg Val Cys
                85                  90                  95

CCG TCG GTG ACA CTG GGA CTG CAG CCC GGC GAG GCA TTC ACC GTC CGC      336
Pro Ser Val Thr Leu Gly Leu Gln Pro Gly Glu Ala Phe Thr Val Arg
            100                 105                 110

AAC ATC GCT TCC ATG GTC CCA CCC TAC GAC AAG ATC AAG TAC GCC GGC      384
Asn Ile Ala Ser Met Val Pro Pro Tyr Asp Lys Ile Lys Tyr Ala Gly
        115                 120                 125

ACA GGG TCC GCC ATC GAG TAC GCC GTG TGC GCG CTC AAG GTG CAG GTC      432
Thr Gly Ser Ala Ile Glu Tyr Ala Val Cys Ala Leu Lys Val Gln Val
    130                 135                 140

ATC GTG GTC ATT GGC CAC AGC TGC TGC GGT GGC ATC AGG GCG CTC CTC      480
Ile Val Val Ile Gly His Ser Cys Cys Gly Gly Ile Arg Ala Leu Leu
145                 150                 155                 160

TCC CTC AAG GAC GGC GCG CCC GAC AAC TTC ACC TTC GTG GAG GAC TGG      528
Ser Leu Lys Asp Gly Ala Pro Asp Asn Phe Thr Phe Val Glu Asp Trp
                165                 170                 175
```

```
GTC AGG ATC GGC AGC CCT GCC AAG AAC AAG GTG AAG AAA GAG CAC GCG         576
Val Arg Ile Gly Ser Pro Ala Lys Asn Lys Val Lys Lys Glu His Ala
            180                 185                 190

TCC GTG CCG TTC GAT GAC CAG TGC TCC ATC CTG GAG AAG GAG GCC GTG         624
Ser Val Pro Phe Asp Asp Gln Cys Ser Ile Leu Glu Lys Glu Ala Val
            195                 200                 205

AAC GTG TCG CTC CAG AAC CTC AAG AGC TAC CCC TTC GTC AAG GAA GGG         672
Asn Val Ser Leu Gln Asn Leu Lys Ser Tyr Pro Phe Val Lys Glu Gly
    210                 215                 220

CTG GCC GGC GGG ACG CTC AAG CTG GTT GGC GCC CAC TAC AGC TTC GTC         720
Leu Ala Gly Gly Thr Leu Lys Leu Val Gly Ala His Tyr Ser Phe Val
225                 230                 235                 240

AAA GGG CAG TTC GTC ACA TGG GAG CCT CCC CAG GAC GCC ATC GAG CGC         768
Lys Gly Gln Phe Val Thr Trp Glu Pro Pro Gln Asp Ala Ile Glu Arg
            245                 250                 255

TTG ACG AGC GGC TTC CAG CAG TTC AAG GTC AAT GTC TAT GAC AAG AAG         816
Leu Thr Ser Gly Phe Gln Gln Phe Lys Val Asn Val Tyr Asp Lys Lys
            260                 265                 270

CCG GAG CTT TTC GGG CCT CTC AAG TCC GGC CAG GCC CCC AAG TAC ATG         864
Pro Glu Leu Phe Gly Pro Leu Lys Ser Gly Gln Ala Pro Lys Tyr Met
            275                 280                 285

GTG TTC GCC TGC TCC GAC TCC CGT GTG TGC CCG TCG GTG ACC CTG GGC         912
Val Phe Ala Cys Ser Asp Ser Arg Val Cys Pro Ser Val Thr Leu Gly
            290                 295                 300

CTG CAG CCC GCG AAG GCC TTC ACC GTT CGC AAC ATC GCC GCC ATG GTC         960
Leu Gln Pro Ala Lys Ala Phe Thr Val Arg Asn Ile Ala Ala Met Val
305                 310                 315                 320

CCA GGC TAC GAC AAG ACC AAG TAC ACC GGC ATC GGG TCC GCC ATC GAG        1008
Pro Gly Tyr Asp Lys Thr Lys Tyr Thr Gly Ile Gly Ser Ala Ile Glu
            325                 330                 335

TAC GCT GTG TGC GCC CTC AAG GTG GAG GTC CTC GTG GTC ATT GGC CAT        1056
Tyr Ala Val Cys Ala Leu Lys Val Glu Val Leu Val Val Ile Gly His
            340                 345                 350

AGC TGC TGC GGT GGC ATC AGG GCG CTC CTC TCC CTC AAG GAC GGC GCG        1104
Ser Cys Cys Gly Gly Ile Arg Ala Leu Leu Ser Leu Lys Asp Gly Ala
            355                 360                 365

CCC GAC AAC TTC CAC TTC GTG GAG GAC TGG GTC AGG ATC GGC AGC CCT        1152
Pro Asp Asn Phe His Phe Val Glu Asp Trp Val Arg Ile Gly Ser Pro
            370                 375                 380

GCC AAG AAC AAG GTG AAG AAA GAG CAC GCG TCC GTG CCG TTC GAT GAC        1200
Ala Lys Asn Lys Val Lys Lys Glu His Ala Ser Val Pro Phe Asp Asp
385                 390                 395                 400

CAG TGC TCC ATC CTG GAG AAG GAG GCC GTG AAC GTG TCG CTC CAG AAC        1248
Gln Cys Ser Ile Leu Glu Lys Glu Ala Val Asn Val Ser Leu Gln Asn
            405                 410                 415

CTC AAG AGC TAC CCC TTG GTC AAG GAA GGG CTG GCC GGC GGG ACG TCA        1296
Leu Lys Ser Tyr Pro Leu Val Lys Glu Gly Leu Ala Gly Gly Thr Ser
            420                 425                 430

AGT GGT TGG CCC CAC TAC GAC TTC GTT AAA GGG CAG TTC GTC ACA TGG        1344
Ser Gly Trp Pro His Tyr Asp Phe Val Lys Gly Gln Phe Val Thr Trp
            435                 440                 445

GAG CCT CCC CAG GAC GCC ATC GAG CGC TTG ACG AGC GGC TTC CAG CAG        1392
Glu Pro Pro Gln Asp Ala Ile Glu Arg Leu Thr Ser Gly Phe Gln Gln
            450                 455                 460

TTC AAG GTC AAT GTC TAT GAC AAG AAG CCG GAG CTT TTC GGG CCT CTC        1440
Phe Lys Val Asn Val Tyr Asp Lys Lys Pro Glu Leu Phe Gly Pro Leu
465                 470                 475                 480

AAG TCC GGC CAG GCC CCC AAG TAC ATG GTG TTC GCC TGC TCC GAC TCC        1488
Lys Ser Gly Gln Ala Pro Lys Tyr Met Val Phe Ala Cys Ser Asp Ser
            485                 490                 495
```

```
CGT GTG TGC CCG TCG GTG ACC CTG CCT GCA GCC GGC GAG GCC TTC ACC        1536
Arg Val Cys Pro Ser Val Thr Leu Pro Ala Ala Gly Glu Ala Phe Thr
            500                 505                 510

GTT CGC AAC ATC GCC GCC ATG GTC CAG GGC TAC GAC AAG ACC AAG TAC        1584
Val Arg Asn Ile Ala Ala Met Val Gln Gly Tyr Asp Lys Thr Lys Tyr
            515                 520                 525

ACC GGC ATC GGG TCC GCC ATC GAG TAC GCT GTG TGC GCC CTC AAG GTG        1632
Thr Gly Ile Gly Ser Ala Ile Glu Tyr Ala Val Cys Ala Leu Lys Val
            530                 535                 540

GAG GTC CTC GTG GTC ATT GGC CAT AGC TGC TGC GGT GGC ATC AGG GCG        1680
Glu Val Leu Val Val Ile Gly His Ser Cys Cys Gly Gly Ile Arg Ala
545                 550                 555                 560

CTC CTC TCA CTC CAG GAC GGC GCA CCT GAC ACC TTC CAC TTC GTC GAG        1728
Leu Leu Ser Leu Gln Asp Gly Ala Pro Asp Thr Phe His Phe Val Glu
                565                 570                 575

GAC TGG GTT AAG ATC GCC TTC ATT GCC AAG ATG AAG GTA AAG AAA GAG        1776
Asp Trp Val Lys Ile Ala Phe Ile Ala Lys Met Lys Val Lys Lys Glu
            580                 585                 590

CAC GCC TCG GTG CCG TTC GAT GAC CAG TGG TCC ATT CTC GAG AAG GAG        1824
His Ala Ser Val Pro Phe Asp Asp Gln Trp Ser Ile Leu Glu Lys Glu
            595                 600                 605

GCC GTG AAC GTG TCC CTG GAG AAC CTC AAG ACC TAC CCC TTC GTC AAG        1872
Ala Val Asn Val Ser Leu Glu Asn Leu Lys Thr Tyr Pro Phe Val Lys
610                 615                 620

GAA GGG CTT GCA AAT GGG ACC CTC AAG CTG ATC GGC GCC CAC TAC GAC        1920
Glu Gly Leu Ala Asn Gly Thr Leu Lys Leu Ile Gly Ala His Tyr Asp
625                 630                 635                 640

TTT GTC TCA GGA GAG TTC CTC ACA TGG AAA AAG TGAAAAACTA GGGCTTTCCG      1973
Phe Val Ser Gly Glu Phe Leu Thr Trp Lys Lys
                645                 650

TTAAGATGGC CGGGCGGCTG AGGACGTAGT AGTATTTATA TATTACTCTA TAACTATACT      2033

ACTACGTACC TACCGATATG CACCCGAGCA ATGTGAATGG GTCGAGTACT ATCTGTTTTC      2093

TGCATCTACA TATATATACC GGATCAACAA TCGCCCAATG TGAATGTAAT AAGCAATATC      2153

ATTTTCTACC ACTTTTCATT CCTAA                                            2178

(2) INFORMATION FOR SEQ ID NO:3:

(i) SEQUENCE CHARACTERISTICS:
        (A) LENGTH: 23 amino acids
        (B) TYPE: amino acid
        (C) STRANDEDNESS: Not Relevant
        (D) TOPOLOGY: linear (ii) MOLECULE TYPE: peptide (xi) SEQUENCE DESCRIPTION: SEQ ID NO:3:

Ala Ala Pro Val Ala Pro Ala Ala Met Asp Ala Ala Val Asp Arg Leu
1               5                   10                  15

Xaa Asp Gly Phe Ala Lys Phe
            20

(2) INFORMATION FOR SEQ ID NO:4:

(i) SEQUENCE CHARACTERISTICS:
        (A) LENGTH: 272 amino acids
        (B) TYPE: amino acid
        (D) TOPOLOGY: linear (ii) MOLECULE TYPE: protein (xi) SEQUENCE DESCRIPTION: SEQ ID NO:4:
```

```
Met Ser Thr Ala Ala Ala Ala Ala Ala Gln Ser Trp Cys Phe Ala
 1               5                  10                  15

Thr Val Thr Pro Arg Ser Arg Ala Thr Val Val Ala Ser Leu Ala Ser
                 20                  25                  30

Pro Ser Pro Ser Ser Ser Ser Ser Asn Ser Ser Asn Leu Pro
             35                  40                  45

Ala Pro Phe Arg Pro Arg Leu Ile Arg Asn Thr Pro Val Phe Ala Ala
 50                  55                  60

Pro Val Ala Pro Ala Ala Met Asp Ala Ala Val Asp Arg Leu Lys Asp
 65                  70                  75                  80

Gly Phe Ala Lys Phe Lys Thr Glu Phe Tyr Asp Lys Lys Pro Glu Leu
                 85                  90                  95

Phe Glu Pro Leu Lys Ala Gly Gln Ala Pro Lys Tyr Met Val Phe Ser
                100                 105                 110

Cys Ala Asp Ser Arg Val Cys Pro Ser Val Thr Met Gly Leu Glu Pro
                115                 120                 125

Gly Glu Ala Phe Thr Val Arg Asn Ile Ala Asn Met Val Pro Ala Tyr
130                 135                 140

Cys Lys Ile Lys His Ala Gly Val Gly Ser Ala Ile Glu Tyr Ala Val
145                 150                 155                 160

Cys Ala Leu Lys Val Glu Leu Ile Val Val Ile Gly His Ser Arg Cys
                165                 170                 175

Gly Gly Ile Lys Ala Leu Leu Ser Leu Lys Asp Gly Ala Pro Asp Ser
                180                 185                 190

Phe His Phe Val Glu Asp Trp Val Arg Thr Gly Phe Pro Ala Lys Lys
                195                 200                 205

Lys Val Gln Thr Glu His Ala Ser Leu Pro Phe Asp Asp Gln Cys Ala
210                 215                 220

Ile Leu Glu Lys Glu Ala Val Asn Gln Ser Leu Glu Asn Leu Lys Thr
225                 230                 235                 240

Tyr Pro Phe Val Lys Glu Gly Ile Ala Asn Gly Thr Leu Lys Leu Val
                245                 250                 255

Gly Gly His Tyr Asp Phe Val Ser Gly Asn Leu Asp Leu Trp Glu Pro
                260                 265                 270

(2) INFORMATION FOR SEQ ID NO:5:

(i) SEQUENCE CHARACTERISTICS:
        (A) LENGTH: 1167 base pairs
        (B) TYPE: nucleic acid
        (C) STRANDEDNESS: single
        (D) TOPOLOGY: linear (ii) MOLECULE TYPE: cDNA to mRNA (ix) FEATURE:
        (A) NAME/KEY: CDS
        (B) LOCATION: 36..851

(xi) SEQUENCE DESCRIPTION: SEQ ID NO:5:

GCCGCGAATT CTTCCGCCGT GCACCGCCTC TCACA ATG TCG ACC GCC GCC GCC          53
                                       Met Ser Thr Ala Ala Ala
                                                          655

GCC GCC GCT GCC CAG AGC TGG TGC TTC GCC ACT GTC ACC CCG CGC TCC        101
Ala Ala Ala Ala Gln Ser Trp Cys Phe Ala Thr Val Thr Pro Arg Ser
            660                 665                 670

CGC GCC ACA GTC GTC GCC AGC CTC GCC TCC CCA TCA CCG TCC TCC TCC        149
Arg Ala Thr Val Val Ala Ser Leu Ala Ser Pro Ser Pro Ser Ser Ser
675                 680                 685
```

| | | |
|---|---|---|
| TCC TCC TCC TCC AAC AGC AGC AAC CTC CCG GCC CCC TTC CGC CCC CGC<br>Ser Ser Ser Ser Asn Ser Ser Asn Leu Pro Ala Pro Phe Arg Pro Arg<br>690                  695                700                705 | 197 |
| CTC ATC CGC AAC ACC CCC GTC TTC GCC GCC CCC GTC GCC CCC GCC GCG<br>Leu Ile Arg Asn Thr Pro Val Phe Ala Ala Pro Val Ala Pro Ala Ala<br>                710                715                720 | 245 |
| ATG GAC GCC GCC GTC GAC CGC CTC AAG GAT GGG TTC GCC AAG TTC AAG<br>Met Asp Ala Ala Val Asp Arg Leu Lys Asp Gly Phe Ala Lys Phe Lys<br>        725                  730                735 | 293 |
| ACC GAG TTC TAT GAC AAG AAG CCG GAG CTC TTC GAG CCG CTC AAG GCC<br>Thr Glu Phe Tyr Asp Lys Lys Pro Glu Leu Phe Glu Pro Leu Lys Ala<br>            740                745                750 | 341 |
| GGC CAG GCA CCC AAG TAC ATG GTG TTC TCG TGC GCC GAC TCT CGC GTG<br>Gly Gln Ala Pro Lys Tyr Met Val Phe Ser Cys Ala Asp Ser Arg Val<br>755                  760                765 | 389 |
| TGC CCG TCG GTG ACC ATG GGC CTG GAG CCC GGC GAG GCC TTC ACC GTC<br>Cys Pro Ser Val Thr Met Gly Leu Glu Pro Gly Glu Ala Phe Thr Val<br>770                  775                780                785 | 437 |
| CGC AAC ATC GCC AAC ATG GTC CCA GCT TAC TGC AAG ATC AAG CAC GCT<br>Arg Asn Ile Ala Asn Met Val Pro Ala Tyr Cys Lys Ile Lys His Ala<br>                790                795                800 | 485 |
| GGC GTC GGG TCG GCC ATC GAG TAC GCC GTC TGC GCC CTC AAG GTC GAA<br>Gly Val Gly Ser Ala Ile Glu Tyr Ala Val Cys Ala Leu Lys Val Glu<br>            805                810                815 | 533 |
| CTC ATC GTG GTG ATT GGC CAC AGC CGC TGC GGT GGA ATC AAG GCC CTC<br>Leu Ile Val Val Ile Gly His Ser Arg Cys Gly Gly Ile Lys Ala Leu<br>820                  825                830 | 581 |
| CTC TCA CTC AAG GAT GGA GCA CCA GAC TCC TTC CAC TTC GTC GAG GAC<br>Leu Ser Leu Lys Asp Gly Ala Pro Asp Ser Phe His Phe Val Glu Asp<br>835                  840                845 | 629 |
| TGG GTC AGG ACC GGT TTC CCC GCC AAG AAG AAG GTT CAG ACC GAG CAC<br>Trp Val Arg Thr Gly Phe Pro Ala Lys Lys Lys Val Gln Thr Glu His<br>850                  855                860                865 | 677 |
| GCC TCG CTG CCT TTC GAT GAC CAA TGC GCC ATC TTG GAG AAG GAG GCC<br>Ala Ser Leu Pro Phe Asp Asp Gln Cys Ala Ile Leu Glu Lys Glu Ala<br>                870                875                880 | 725 |
| GTG AAC CAA TCC CTG GAG AAC CTC AAG ACC TAC CCG TTC GTC AAG GAG<br>Val Asn Gln Ser Leu Glu Asn Leu Lys Thr Tyr Pro Phe Val Lys Glu<br>            885                890                895 | 773 |
| GGG ATC GCC AAC GGC ACC CTC AAG CTC GTC GGC GGC CAC TAC GAC TTC<br>Gly Ile Ala Asn Gly Thr Leu Lys Leu Val Gly Gly His Tyr Asp Phe<br>900                  905                910 | 821 |
| GTC TCC GGC AAC TTG GAC TTA TGG GAG CCC TAAATCCGAC CGTCCGTCCG<br>Val Ser Gly Asn Leu Asp Leu Trp Glu Pro<br>915                  920 | 871 |
| TTCAGTTCGT CAGTTTACGC CAACGCTTTT GCATAAGTAC TACCTGAGGA TATCGTCCCC | 931 |
| GATCATCGAT GTGAACGCGT GGAGTACTAC TACGTACGTA CCGGATGGTT CGATATATGT | 991 |
| GAATGCTGTA TTAAGTAATA ACAAGAAATA TATCTCCTCT ACTTTTTCCT GACGCGGAGT | 1051 |
| TGTACTGCCT ATGATGCATA ATTTGATCGC AGTGTGATCA AAAGACATCA GCTATAATGT | 1111 |
| CTTAATAATA TTATTATGAA GAGTTTACCT TTTTACTAAA AAAAAAAAA AAAAAA | 1167 |

(2) INFORMATION FOR SEQ ID NO:6:

(i) SEQUENCE CHARACTERISTICS:
        (A) LENGTH: 655 amino acids
        (B) TYPE: amino acid
        (D) TOPOLOGY: linear (ii) MOLECULE TYPE: protein (xi) SEQUENCE DESCRIPTION: SEQ ID NO:6:

```
Met Tyr Thr Leu Pro Val Arg Ala Thr Thr Ser Ser Ile Val Ala Ser
 1               5                  10                  15
Leu Ala Thr Pro Ala Pro Ser Ser Ser Gly Ser Gly Arg Pro Arg
            20                  25                  30
Leu Arg Leu Ile Arg Asn Ala Pro Val Phe Ala Ala Pro Ala Thr Val
            35                  40                  45
Val Gly Met Asp Pro Thr Val Glu Arg Leu Lys Ser Gly Phe Gln Lys
        50                  55                  60
Phe Lys Thr Glu Val Tyr Asp Lys Lys Pro Glu Leu Phe Glu Pro Leu
 65                  70                  75                  80
Lys Ser Gly Gln Ser Pro Arg Tyr Met Val Phe Ala Cys Ser Asp Ser
                85                  90                  95
Arg Val Cys Pro Ser Val Thr Leu Gly Leu Gln Pro Gly Glu Ala Phe
                100                 105                 110
Thr Val Arg Asn Ile Ala Ser Met Val Pro Pro Tyr Asp Lys Ile Lys
            115                 120                 125
Tyr Ala Gly Thr Gly Ser Ala Ile Glu Tyr Ala Val Cys Ala Leu Lys
        130                 135                 140
Val Gln Val Ile Val Ile Gly His Ser Cys Cys Gly Gly Ile Arg
145                 150                 155                 160
Ala Leu Leu Ser Leu Lys Asp Gly Ala Pro Asp Asn Phe Thr Phe Val
                165                 170                 175
Glu Asp Trp Val Arg Ile Gly Ser Pro Ala Lys Asn Lys Val Lys Lys
            180                 185                 190
Glu His Ala Ser Val Pro Phe Asp Asp Gln Cys Ser Ile Leu Glu Lys
            195                 200                 205
Glu Ala Val Asn Val Ser Leu Gln Asn Leu Lys Ser Tyr Pro Phe Val
        210                 215                 220
Lys Glu Gly Leu Ala Gly Thr Leu Lys Leu Val Gly Ala His Tyr
225                 230                 235                 240
Ser Phe Val Lys Gly Gln Phe Val Thr Trp Glu Pro Gln Asp Ala
                245                 250                 255
Ile Glu Arg Leu Thr Ser Gly Phe Gln Gln Phe Lys Val Asn Val Tyr
            260                 265                 270
Asp Lys Lys Pro Glu Leu Phe Gly Pro Leu Lys Ser Gly Gln Ala Pro
        275                 280                 285
Lys Tyr Met Val Phe Ala Cys Ser Asp Ser Arg Val Cys Pro Ser Val
        290                 295                 300
Thr Leu Gly Leu Gln Pro Ala Lys Ala Phe Thr Val Arg Asn Ile Ala
305                 310                 315                 320
Ala Met Val Pro Gly Tyr Asp Lys Thr Lys Tyr Thr Gly Ile Gly Ser
                325                 330                 335
Ala Ile Glu Tyr Ala Val Cys Ala Leu Lys Val Glu Val Leu Val Val
            340                 345                 350
Ile Gly His Ser Cys Cys Gly Gly Ile Arg Ala Leu Leu Ser Leu Lys
            355                 360                 365
Asp Gly Ala Pro Asp Asn Phe His Phe Val Glu Asp Trp Val Arg Ile
        370                 375                 380
Gly Ser Pro Ala Lys Asn Lys Val Lys Glu His Ala Ser Val Pro
385                 390                 395                 400
Phe Asp Asp Gln Cys Ser Ile Leu Glu Lys Glu Ala Val Asn Val Ser
                405                 410                 415
```

```
Leu Gln Asn Leu Lys Ser Tyr Pro Leu Val Lys Glu Gly Leu Ala Gly
        420                 425                 430

Gly Thr Ser Ser Gly Trp Pro His Tyr Asp Phe Val Lys Gly Gln Phe
        435                 440                 445

Val Thr Trp Glu Pro Pro Gln Asp Ala Ile Glu Arg Leu Thr Ser Gly
450                 455                 460

Phe Gln Gln Phe Lys Val Asn Val Tyr Asp Lys Lys Pro Glu Leu Phe
465                 470                 475                 480

Gly Pro Leu Lys Ser Gly Gln Ala Pro Lys Tyr Met Val Phe Ala Cys
        485                 490                 495

Ser Asp Ser Arg Val Ser Pro Ser Val Thr Leu Gly Leu Gln Pro Gly
        500                 505                 510

Glu Ala Phe Thr Val Arg Asn Ile Ala Ala Met Val Pro Gly Tyr Asp
        515                 520                 525

Lys Thr Lys Tyr Thr Gly Ile Gly Ser Ala Ile Glu Tyr Ala Val Cys
530                 535                 540

Ala Leu Lys Val Glu Val Leu Val Ile Gly His Ser Cys Cys Gly
545                 550                 555                 560

Gly Ile Arg Ala Leu Leu Ser Leu Gln Asp Gly Ala Pro Asp Thr Phe
            565                 570                 575

His Phe Val Glu Asp Trp Val Lys Ile Ala Phe Ile Ala Lys Met Lys
        580                 585                 590

Val Lys Lys Glu His Ala Ser Val Pro Phe Asp Asp Gln Trp Ser Ile
        595                 600                 605

Leu Glu Lys Glu Ala Val Asn Val Ser Leu Glu Asn Leu Lys Thr Tyr
        610                 615                 620

Pro Phe Val Lys Glu Gly Leu Ala Asn Gly Thr Leu Lys Leu Ile Gly
625                 630                 635                 640

Ala His Tyr Asp Phe Val Ser Gly Glu Phe Leu Thr Trp Lys Lys
            645                 650                 655

(2) INFORMATION FOR SEQ ID NO:7:

(i) SEQUENCE CHARACTERISTICS:
        (A) LENGTH: 2190 base pairs
        (B) TYPE: nucleic acid
        (C) STRANDEDNESS: single
        (D) TOPOLOGY: linear (ii) MOLECULE TYPE: other nucleic acid (ix) FEATURE:
        (A) NAME/KEY: CDS
        (B) LOCATION: 1..1965

(xi) SEQUENCE DESCRIPTION: SEQ ID NO:7:

ATG TAC ACA TTG CCC GTC CGT GCC ACC ACA TCC AGC ATC GTC GCC AGC     48
Met Tyr Thr Leu Pro Val Arg Ala Thr Thr Ser Ser Ile Val Ala Ser
        275                 280                 285

CTC GCC ACC CCC GCG CCG TCC TCC TCC TCC GGC TCC GGC CGC CCC AGG     96
Leu Ala Thr Pro Ala Pro Ser Ser Ser Ser Gly Ser Gly Arg Pro Arg
        290                 295                 300

CTC AGG CTC ATC CGG AAC GCC CCC GTC TTC GCC GCC CCC GCC ACC GTC    144
Leu Arg Leu Ile Arg Asn Ala Pro Val Phe Ala Ala Pro Ala Thr Val
305                 310                 315                 320

GTG GGC ATG GAC CCC ACC GTC GAG CGC TTG AAG AGC GGG TTC CAG AAG    192
Val Gly Met Asp Pro Thr Val Glu Arg Leu Lys Ser Gly Phe Gln Lys
            325                 330                 335

TTC AAG ACC GAG GTC TAT GAC AAG AAG CCG GAG CTG TTC GAG CCT CTC    240
Phe Lys Thr Glu Val Tyr Asp Lys Lys Pro Glu Leu Phe Glu Pro Leu
```

-continued

```
                340                 345                 350
AAG TCC GGC CAG AGC CCC AGG TAC ATG GTG TTC GCC TGC TCC GAC TCC        288
Lys Ser Gly Gln Ser Pro Arg Tyr Met Val Phe Ala Cys Ser Asp Ser
        355                 360                 365

CGC GTG TGC CCG TCG GTG ACA CTG GGA CTG CAG CCC GGC GAG GCA TTC        336
Arg Val Cys Pro Ser Val Thr Leu Gly Leu Gln Pro Gly Glu Ala Phe
        370                 375                 380

ACC GTC CGC AAC ATC GCT TCC ATG GTC CCA CCC TAC GAC AAG ATC AAG        384
Thr Val Arg Asn Ile Ala Ser Met Val Pro Pro Tyr Asp Lys Ile Lys
385                 390                 395                 400

TAC GCC GGC ACA GGG TCC GCC ATC GAG TAC GCC GTG TGC GCG CTC AAG        432
Tyr Ala Gly Thr Gly Ser Ala Ile Glu Tyr Ala Val Cys Ala Leu Lys
                405                 410                 415

GTG CAG GTC ATC GTG GTC ATT GGC CAC AGC TGC TGC GGT GGC ATC AGG        480
Val Gln Val Ile Val Val Ile Gly His Ser Cys Cys Gly Gly Ile Arg
        420                 425                 430

GCG CTC CTC TCC CTC AAG GAC GGC GCG CCC GAC AAC TTC ACC TTC GTG        528
Ala Leu Leu Ser Leu Lys Asp Gly Ala Pro Asp Asn Phe Thr Phe Val
        435                 440                 445

GAG GAC TGG GTC AGG ATC GGC AGC CCT GCC AAG AAC AAG GTG AAG AAA        576
Glu Asp Trp Val Arg Ile Gly Ser Pro Ala Lys Asn Lys Val Lys Lys
450                 455                 460

GAG CAC GCG TCC GTG CCG TTC GAT GAC CAG TGC TCC ATC CTG GAG AAG        624
Glu His Ala Ser Val Pro Phe Asp Asp Gln Cys Ser Ile Leu Glu Lys
465                 470                 475                 480

GAG GCC GTG AAC GTG TCG CTC CAG AAC CTC AAG AGC TAC CCC TTC GTC        672
Glu Ala Val Asn Val Ser Leu Gln Asn Leu Lys Ser Tyr Pro Phe Val
                485                 490                 495

AAG GAA GGG CTG GCC GGC GGG ACG CTC AAG CTG GTT GGC GCC CAC TAC        720
Lys Glu Gly Leu Ala Gly Gly Thr Leu Lys Leu Val Gly Ala His Tyr
        500                 505                 510

AGC TTC GTC AAA GGG CAG TTC GTC ACA TGG GAG CCT CCC CAG GAC GCC        768
Ser Phe Val Lys Gly Gln Phe Val Thr Trp Glu Pro Pro Gln Asp Ala
        515                 520                 525

ATC GAG CGC TTG ACG AGC GGC TTC CAG CAG TTC AAG GTC AAT GTC TAT        816
Ile Glu Arg Leu Thr Ser Gly Phe Gln Gln Phe Lys Val Asn Val Tyr
530                 535                 540

GAC AAG AAG CCG GAG CTT TTC GGG CCT CTC AAG TCC GGC CAG GCC CCC        864
Asp Lys Lys Pro Glu Leu Phe Gly Pro Leu Lys Ser Gly Gln Ala Pro
545                 550                 555                 560

AAG TAC ATG GTG TTC GCC TGC TCC GAC TCC CGT GTG TGC CCG TCG GTG        912
Lys Tyr Met Val Phe Ala Cys Ser Asp Ser Arg Val Cys Pro Ser Val
                565                 570                 575

ACC CTG GGC CTG CAG CCC GCG AAG GCC TTC ACC GTT CGC AAC ATC GCC        960
Thr Leu Gly Leu Gln Pro Ala Lys Ala Phe Thr Val Arg Asn Ile Ala
        580                 585                 590

GCC ATG GTC CCA GGC TAC GAC AAG ACC AAG TAC ACC GGC ATC GGG TCC       1008
Ala Met Val Pro Gly Tyr Asp Lys Thr Lys Tyr Thr Gly Ile Gly Ser
        595                 600                 605

GCC ATC GAG TAC GCT GTG TGC GCC CTC AAG GTG GAG GTC CTC GTG GTC       1056
Ala Ile Glu Tyr Ala Val Cys Ala Leu Lys Val Glu Val Leu Val Val
        610                 615                 620

ATT GGC CAT AGC TGC TGC GGT GGC ATC AGG GCG CTC CTC TCC CTC AAG       1104
Ile Gly His Ser Cys Cys Gly Gly Ile Arg Ala Leu Leu Ser Leu Lys
625                 630                 635                 640

GAC GGC GCG CCC GAC AAC TTC CAC TTC GTG GAG GAC TGG GTC AGG ATC       1152
Asp Gly Ala Pro Asp Asn Phe His Phe Val Glu Asp Trp Val Arg Ile
        645                 650                 655

GGC AGC CCT GCC AAG AAC AAG GTG AAG AAA GAG CAC GCG TCC GTG CCG       1200
Gly Ser Pro Ala Lys Asn Lys Val Lys Lys Glu His Ala Ser Val Pro
```

-continued

```
                660                 665                 670
TTC GAT GAC CAG TGC TCC ATC CTG GAG AAG GAG GCC GTG AAC GTG TCG        1248
Phe Asp Asp Gln Cys Ser Ile Leu Glu Lys Glu Ala Val Asn Val Ser
            675                 680                 685

CTC CAG AAC CTC AAG AGC TAC CCC TTG GTC AAG GAA GGG CTG GCC GGC        1296
Leu Gln Asn Leu Lys Ser Tyr Pro Leu Val Lys Glu Gly Leu Ala Gly
        690                 695                 700

GGG ACG TCA AGT GGT TGG CCC CAC TAC GAC TTC GTT AAA GGG CAG TTC        1344
Gly Thr Ser Ser Gly Trp Pro His Tyr Asp Phe Val Lys Gly Gln Phe
705                 710                 715                 720

GTC ACA TGG GAG CCT CCC CAG GAC GCC ATC GAG CGC TTG ACG AGC GGC        1392
Val Thr Trp Glu Pro Pro Gln Asp Ala Ile Glu Arg Leu Thr Ser Gly
                725                 730                 735

TTC CAG CAG TTC AAG GTC AAT GTC TAT GAC AAG AAG CCG GAG CTT TTC        1440
Phe Gln Gln Phe Lys Val Asn Val Tyr Asp Lys Lys Pro Glu Leu Phe
            740                 745                 750

GGG CCT CTC AAG TCC GGC CAG GCC CCC AAG TAC ATG GTG TTC GCC TGC        1488
Gly Pro Leu Lys Ser Gly Gln Ala Pro Lys Tyr Met Val Phe Ala Cys
        755                 760                 765

TCC GAC TCC CGT GTG TCC CCG TCG GTG ACC CTG GGC CTG CAG CCC GGC        1536
Ser Asp Ser Arg Val Ser Pro Ser Val Thr Leu Gly Leu Gln Pro Gly
770                 775                 780

GAG GCC TTC ACC GTT CGC AAC ATC GCC GCC ATG GTC CCC GGC TAC GAC        1584
Glu Ala Phe Thr Val Arg Asn Ile Ala Ala Met Val Pro Gly Tyr Asp
785                 790                 795                 800

AAG ACC AAG TAC ACC GGC ATC GGG TCC GCC ATC GAG TAC GCT GTG TGC        1632
Lys Thr Lys Tyr Thr Gly Ile Gly Ser Ala Ile Glu Tyr Ala Val Cys
                805                 810                 815

GCC CTC AAG GTG GAG GTC CTC GTG GTC ATT GGC CAT AGC TGC TGC GGT        1680
Ala Leu Lys Val Glu Val Leu Val Val Ile Gly His Ser Cys Cys Gly
            820                 825                 830

GGC ATC AGG GCG CTC CTC TCA CTC CAG GAC GGC GCA CCT GAC ACC TTC        1728
Gly Ile Arg Ala Leu Leu Ser Leu Gln Asp Gly Ala Pro Asp Thr Phe
        835                 840                 845

CAC TTC GTC GAG GAC TGG GTT AAG ATC GCC TTC ATT GCC AAG ATG AAG        1776
His Phe Val Glu Asp Trp Val Lys Ile Ala Phe Ile Ala Lys Met Lys
850                 855                 860

GTA AAG AAA GAG CAC GCC TCG GTG CCG TTC GAT GAC CAG TGG TCC ATT        1824
Val Lys Lys Glu His Ala Ser Val Pro Phe Asp Asp Gln Trp Ser Ile
865                 870                 875                 880

CTC GAG AAG GAG GCC GTG AAC GTG TCC CTG GAG AAC CTC AAG ACC TAC        1872
Leu Glu Lys Glu Ala Val Asn Val Ser Leu Glu Asn Leu Lys Thr Tyr
                885                 890                 895

CCC TTC GTC AAG GAA GGG CTT GCA AAT GGG ACC CTC AAG CTG ATC GGC        1920
Pro Phe Val Lys Glu Gly Leu Ala Asn Gly Thr Leu Lys Leu Ile Gly
            900                 905                 910

GCC CAC TAC GAC TTT GTC TCA GGA GAG TTC CTC ACA TGG AAA AAG            1965
Ala His Tyr Asp Phe Val Ser Gly Glu Phe Leu Thr Trp Lys Lys
        915                 920                 925

TGAAAAACTA GGGCTAAGGC AATTCTACCG GCCCGCCGAC TCCTGCATCA TCATAAATAT     2025

ATATACTCTA TAACTATACT ACTACGTACC TACCGATATG CACCCGAGCA ATGTGAATGC     2085

GTCGAGTACT ATCTGTTTTC TGCATCTACA TATATATACC GGATCAACAA TCGCCCAATG     2145

TGAATGTAAT AAGCAATATC ATTTTCTACC ACTTTTCATT CCTAA                     2190
```

(2) INFORMATION FOR SEQ ID NO:8:

(i) SEQUENCE CHARACTERISTICS:
        (A) LENGTH: 546 amino acids
        (B) TYPE: amino acid (D) TOPOLOGY: linear (ii) MOLECULE TYPE: protein (xi) SEQUENCE DESCRIPTION: SEQ ID NO:8:

```
Met Tyr Thr Leu Pro Val Arg Ala Thr Thr Ser Ser Ile Val Ala Ser
 1               5                  10                  15

Leu Ala Thr Pro Ala Pro Ser Ser Ser Gly Ser Gly Arg Pro Arg
            20                  25                  30

Leu Arg Leu Ile Arg Asn Ala Pro Val Phe Ala Ala Pro Ala Thr Val
            35                  40                  45

Cys Lys Arg Asp Gly Gly Gln Leu Arg Ser Gln Thr Arg Glu Ile Glu
            50                  55                  60

Arg Glu Arg Lys Gly Gly His Pro Pro Ala Gly Gly His Lys Arg Gly
 65                  70                  75                  80

Gly Glu Arg Gly Gln Arg Arg Gly Gly Glu Glu Glu Asp Glu Gln
            85                  90                  95

Leu Pro Leu Pro Ser Glu Lys Lys Gly Gly Ala Ser Glu Gly Glu Ala
                100                 105                 110

Val His Arg Tyr Pro His Leu Val Thr Pro Ser Glu Pro Glu Ala Leu
            115                 120                 125

Gln Pro Pro Pro Pro Ser Lys Ala Ser Ser Lys Gly Met Asp Pro
            130                 135                 140

Thr Val Glu Arg Leu Lys Ser Gly Phe Gln Lys Phe Lys Thr Glu Val
145                 150                 155                 160

Tyr Asp Lys Lys Pro Glu Leu Phe Glu Pro Leu Lys Ser Gly Gln Ser
                165                 170                 175

Pro Arg Tyr Met Val Phe Ala Cys Ser Asp Ser Arg Val Cys Pro Ser
            180                 185                 190

Val Thr Leu Gly Leu Gln Pro Gly Glu Ala Phe Thr Val Arg Asn Ile
            195                 200                 205

Ala Ser Met Val Pro Pro Tyr Asp Lys Ile Lys Tyr Ala Gly Thr Gly
            210                 215                 220

Ser Ala Ile Glu Tyr Ala Val Cys Ala Leu Lys Val Gln Val Ile Val
225                 230                 235                 240

Val Ile Gly His Ser Cys Cys Gly Gly Ile Arg Ala Leu Leu Ser Leu
            245                 250                 255

Lys Asp Gly Ala Pro Asp Asn Phe Thr Phe Val Glu Asp Trp Val Arg
            260                 265                 270

Ile Gly Ser Pro Ala Lys Asn Lys Val Lys Glu His Ala Ser Val
            275                 280                 285

Pro Phe Asp Asp Gln Cys Ser Ile Leu Glu Lys Glu Ala Val Asn Val
            290                 295                 300

Ser Leu Gln Asn Leu Lys Ser Tyr Pro Phe Val Lys Glu Gly Leu Ala
305                 310                 315                 320

Gly Gly Thr Leu Lys Leu Val Gly Ala His Ser His Phe Val Lys Gly
            325                 330                 335

Gln Phe Val Thr Trp Glu Pro Pro Gln Asp Ala Ile Glu Arg Leu Thr
            340                 345                 350

Ser Gly Phe Gln Gln Phe Lys Val Asn Val Tyr Asp Lys Lys Pro Glu
            355                 360                 365

Leu Phe Gly Pro Leu Lys Ser Gly Gln Ala Pro Lys Tyr Met Val Phe
            370                 375                 380

Ala Cys Ser Asp Ser Arg Val Cys Pro Ser Val Thr Leu Gly Leu Gln
385                 390                 395                 400
```

```
Pro Gly Glu Ala Phe Thr Val Arg Asn Ile Ala Ala Met Val Pro Gly
            405                 410                 415

Tyr Asp Lys Thr Lys Tyr Thr Gly Ile Gly Ser Ala Ile Glu Tyr Ala
            420                 425                 430

Val Cys Ala Leu Lys Val Glu Val Leu Val Val Ile Gly His Ser Cys
            435                 440                 445

Cys Gly Gly Ile Arg Ala Leu Leu Ser Leu Gln Gly Thr Gly Ala Ala
    450                 455                 460

Tyr Thr Phe His Phe Val Glu Asp Trp Val Lys Ile Gly Phe Ile Ala
465                 470                 475                 480

Lys Met Lys Val Lys Lys Glu His Ala Ser Val Pro Phe Asp Asp Gln
            485                 490                 495

Cys Ser Ile Leu Glu Lys Glu Ala Val Asn Val Ser Leu Glu Asn Leu
            500                 505                 510

Lys Thr Tyr Pro Phe Val Lys Glu Gly Leu Ala Asn Gly Thr Leu Lys
            515                 520                 525

Leu Ile Gly Ala His Tyr Asp Phe Val Ser Gly Glu Phe Leu Thr Trp
530                 535                 540

Lys Lys
545

(2) INFORMATION FOR SEQ ID NO:9:

(i) SEQUENCE CHARACTERISTICS:
        (A) LENGTH: 1935 base pairs
        (B) TYPE: nucleic acid
        (C) STRANDEDNESS: single
        (D) TOPOLOGY: linear (ii) MOLECULE TYPE: other nucleic acid (ix) FEATURE:
        (A) NAME/KEY: CDS
        (B) LOCATION: 1..1638

(xi) SEQUENCE DESCRIPTION: SEQ ID NO:9:

ATG TAC ACA TTG CCC GTC CGT GCC ACC ACA TCC AGC ATC GTC GCC AGC          48
Met Tyr Thr Leu Pro Val Arg Ala Thr Thr Ser Ser Ile Val Ala Ser
            660                 665                 670

CTC GCC ACC CCC GCG CCG TCC TCC TCC TCC GGC TCC GGC CGC CCC AGG          96
Leu Ala Thr Pro Ala Pro Ser Ser Ser Ser Gly Ser Gly Arg Pro Arg
        675                 680                 685

CTC AGG CTC ATC CGG AAC GCC CCC GTC TTC GCC GCC CCC GCC ACC GTC         144
Leu Arg Leu Ile Arg Asn Ala Pro Val Phe Ala Ala Pro Ala Thr Val
    690                 695                 700

TGT AAA CGG GAC GGC GGG CAG CTG AGG AGT CAA ACG AGA GAG ATC GAG         192
Cys Lys Arg Asp Gly Gly Gln Leu Arg Ser Gln Thr Arg Glu Ile Glu
705                 710                 715

AGA GAA AGA AAG GGA GGG CAT CCA CCA GCC GGC GGG CAT AAG AGG GGA         240
Arg Glu Arg Lys Gly Gly His Pro Pro Ala Gly Gly His Lys Arg Gly
720                 725                 730                 735

GGA GAG AGA GGC CAG AGA AGA GGA GGA GAA GAA GAA GAA GAT GAG CAG         288
Gly Glu Arg Gly Gln Arg Arg Gly Gly Glu Glu Glu Glu Asp Glu Gln
            740                 745                 750

CTG CCT CTG CCT TCC GAA AAA AAA GGA GGG GCC AGC GAA GGA GAA GCC         336
Leu Pro Leu Pro Ser Glu Lys Lys Gly Gly Ala Ser Glu Gly Glu Ala
            755                 760                 765

GTC CAC AGA TAC CCC CAC CTC GTC ACT CCT TCA GAA CCA GAA GCC CTC         384
Val His Arg Tyr Pro His Leu Val Thr Pro Ser Glu Pro Glu Ala Leu
        770                 775                 780
```

```
CAA CCT CCA CCT CCT CCC TCC AAG GCT TCC TCC AAG GGC ATG GAC CCC       432
Gln Pro Pro Pro Pro Ser Lys Ala Ser Ser Lys Gly Met Asp Pro
785                 790                 795

ACC GTC GAG CGC TTG AAG AGC GGG TTC CAG AAG TTC AAG ACC GAG GTC       480
Thr Val Glu Arg Leu Lys Ser Gly Phe Gln Lys Phe Lys Thr Glu Val
800                 805                 810                 815

TAT GAC AAG AAG CCG GAG CTG TTC GAG CCT CTC AAG TCC GGC CAG AGC       528
Tyr Asp Lys Lys Pro Glu Leu Phe Glu Pro Leu Lys Ser Gly Gln Ser
                820                 825                 830

CCC AGG TAC ATG GTG TTC GCC TGC TCC GAC TCC CGC GTG TGC CCG TCG       576
Pro Arg Tyr Met Val Phe Ala Cys Ser Asp Ser Arg Val Cys Pro Ser
            835                 840                 845

GTG ACA CTG GGA CTG CAG CCC GGC GAG GCA TTC ACC GTC CGC AAC ATC       624
Val Thr Leu Gly Leu Gln Pro Gly Glu Ala Phe Thr Val Arg Asn Ile
        850                 855                 860

GCT TCC ATG GTC CCA CCC TAC GAC AAG ATC AAG TAC GCC GGC ACA GGG       672
Ala Ser Met Val Pro Pro Tyr Asp Lys Ile Lys Tyr Ala Gly Thr Gly
865                 870                 875

TCC GCC ATC GAG TAC GCC GTG TGC GCG CTC AAG GTG CAG GTC ATC GTG       720
Ser Ala Ile Glu Tyr Ala Val Cys Ala Leu Lys Val Gln Val Ile Val
880                 885                 890                 895

GTC ATT GGC CAC AGC TGC TGC GGT GGC ATC AGG GCG CTC CTC TCC CTC       768
Val Ile Gly His Ser Cys Cys Gly Gly Ile Arg Ala Leu Leu Ser Leu
                900                 905                 910

AAG GAC GGC GCG CCC GAC AAC TTC ACC TTC GTG GAG GAC TGG GTC AGG       816
Lys Asp Gly Ala Pro Asp Asn Phe Thr Phe Val Glu Asp Trp Val Arg
            915                 920                 925

ATC GGC AGC CCT GCC AAG AAC AAG GTG AAG AAA GAG CAC GCG TCC GTG       864
Ile Gly Ser Pro Ala Lys Asn Lys Val Lys Lys Glu His Ala Ser Val
        930                 935                 940

CCG TTC GAT GAC CAG TGC TCC ATC CTG GAG AAG GAG GCC GTG AAC GTG       912
Pro Phe Asp Asp Gln Cys Ser Ile Leu Glu Lys Glu Ala Val Asn Val
945                 950                 955

TCG CTC CAG AAC CTC AAG AGC TAC CCC TTC GTC AAG GAA GGG CTG GCC       960
Ser Leu Gln Asn Leu Lys Ser Tyr Pro Phe Val Lys Glu Gly Leu Ala
960                 965                 970                 975

GGC GGG ACG CTC AAG CTG GTT GGC GCC CAC TCA CAC TTC GTC AAA GGG      1008
Gly Gly Thr Leu Lys Leu Val Gly Ala His Ser His Phe Val Lys Gly
                980                 985                 990

CAG TTC GTC ACA TGG GAG CCT CCC CAG GAC GCC ATC GAG CGC TTG ACG      1056
Gln Phe Val Thr Trp Glu Pro Pro Gln Asp Ala Ile Glu Arg Leu Thr
            995                 1000                1005

AGC GGC TTC CAG CAG TTC AAG GTC AAT GTC TAT GAC AAG AAG CCG GAG      1104
Ser Gly Phe Gln Gln Phe Lys Val Asn Val Tyr Asp Lys Lys Pro Glu
        1010                1015                1020

CTT TTC GGG CCT CTC AAG TCC GGC CAG GCC CCC AAG TAC ATG GTG TTC      1152
Leu Phe Gly Pro Leu Lys Ser Gly Gln Ala Pro Lys Tyr Met Val Phe
1025                1030                1035

GCC TGC TCC GAC TCC CGT GTG TGC CCG TCG GTG ACC CTG GGC CTG CAG      1200
Ala Cys Ser Asp Ser Arg Val Cys Pro Ser Val Thr Leu Gly Leu Gln
1040                1045                1050                1055

CCG GGC GAG GCC TTC ACC GTT CGC AAC ATC GCC GCC ATG GTC CCA GGC      1248
Pro Gly Glu Ala Phe Thr Val Arg Asn Ile Ala Ala Met Val Pro Gly
                1060                1065                1070

TAC GAC AAG ACC AAG TAC ACC GGC ATC GGG TCC GCC ATC GAG TAC GCT      1296
Tyr Asp Lys Thr Lys Tyr Thr Gly Ile Gly Ser Ala Ile Glu Tyr Ala
            1075                1080                1085

GTG TGC GCC CTC AAG GTG GAG GTC CTC GTG GTC ATT GGC CAT AGC TGC      1344
Val Cys Ala Leu Lys Val Glu Val Leu Val Val Ile Gly His Ser Cys
        1090                1095                1100
```

-continued

```
TGC GGT GGC ATC AGG GCG CTC CTC TCC CTC CAA GGA ACC GGC GCA GCC          1392
Cys Gly Gly Ile Arg Ala Leu Leu Ser Leu Gln Gly Thr Gly Ala Ala
    1105                1110                1115

TAC ACC TTC CAC TTC GTC GAG GAC TGG GTT AAG ATC GGC TTC ATT GCC          1440
Tyr Thr Phe His Phe Val Glu Asp Trp Val Lys Ile Gly Phe Ile Ala
1120                1125                1130                1135

AAG ATG AAG GTA AAG AAA GAG CAC GCC TCG GTG CCG TTC GAT GAC CAG          1488
Lys Met Lys Val Lys Lys Glu His Ala Ser Val Pro Phe Asp Asp Gln
                1140                1145                1150

TGC TCC ATT CTC GAG AAG GAG GCC GTG AAC GTG TCC CTG GAG AAC CTC          1536
Cys Ser Ile Leu Glu Lys Glu Ala Val Asn Val Ser Leu Glu Asn Leu
            1155                1160                1165

AAG ACC TAC CCC TTC GTC AAG GAA GGG CTT GCA AAT GGG ACC CTC AAG          1584
Lys Thr Tyr Pro Phe Val Lys Glu Gly Leu Ala Asn Gly Thr Leu Lys
        1170                1175                1180

CTG ATC GGC GCC CAC TAC GAC TTT GTC TCA GGA GAG TTC CTC ACA TGG          1632
Leu Ile Gly Ala His Tyr Asp Phe Val Ser Gly Glu Phe Leu Thr Trp
    1185                1190                1195

AAA AAG TGAAAAACTA GGGCTAAGGC AATTCTACCG GCCCGCCGAC TCTGCATCAT           1688
Lys Lys
1200

CATAATATAT ATACTATAAC TATACTACTA GCTACCTACC GATAGTCACC CGAGCAATGT        1748

GAATGCGTCG AGTACTATCT GTTTTCTGCA TCTACATATA TATACCGGAT CAACAATCGC        1808

CCAATGTGAA TGTAATAAGC AATATCATTT TCTACCACTT TTCATTCCTA ACGCTGAGGC        1868

TTTTTATGTA CTATATCTTA TATGATGAAT AATAATATGA CCGCCTTGTG ATCTAAAAAA       1928

AAAAAAA                                                                  1935
```

DNA ENCODING CARBONIC ANHYDRASE

This is a U.S. National Stage Application of PCT/JP94/01814 filed Oct. 27,1994.

TECHNICAL FIELD

The present invention relates to a novel DNA which encodes carbonic anhydrase of a monocotyledon.

BACKGROUND ART

Carbonic anhydrase (carbonic dehydratase) is an enzyme widely occurring in animals and plants, which catalyzes the following reaction.

$$CO_2 + H_2O \leftarrow \rightarrow H^+ + HCO_3^-$$

In $C_3$ plants, it is thought that carbonic anhydrase plays a role in preventing evaporation of $CO_2$ from chloroplasts by converting $CO_2$ to carbonate ion. One of substrates of ribulose bisphosphate carboxylase (Rubisco) which is an enzyme for carbon dioxide fixation is $CO_2$. Thus, it is thought that carbonic anhydrase supplies the substrate of Rubisco. Localization of carbonic anhydrase in cells of higher plants varies depending on the type of photosynthesis of the plant. In $C_3$ plants, carbonic anhydrase activity is found in chloroplasts and in $C_4$ plants, carbonic anhydrase activity is mainly found in cytoplasm of mesophyll cells.

As mentioned above, carbonic anhydrase catalyzes the reaction by which equilibrium between $CO_2$ and hydrogen carbonate ion ($HCO_3^-$) in a solution is maintained. Although this equilibrium is reached under natural conditions, it takes a long time to reach the equilibrium if the enzyme does not participate. Therefore, if this enzyme is introduced by genetic engineering technique into a $C_3$ plant in which the enzyme is not localized in cytoplasm, it is thought that the reaction to reach the equilibrium between $CO_2$ and $HCO_3^-$ is promoted and so the substrate of the enzyme carrying out carbon dioxide fixation is efficiently supplied, so that the ability to carry out carbon dioxide fixation of the plant is promoted.

Recently, it was reported that phosphoenol pyruvate carboxylase (PEPC) which is an enzyme catalyzing the first carbon dioxide fixation reaction of $C_4$ plants was introduced into a $C_3$ plant by genetic engineering technique (Hudspeth, R. L. et al., (1992), Plant Physiol. 98:485–464; Katsura IZUI et al., (1993), Plant Cell Technology 5: 74–82). The substrate of this enzyme is $HCO_3^-$. Since carbonic anhydrase does not exist in cytoplasm of $C_3$ plants, in order that PEPC expressed in the cytoplasm efficiently functions, it is necessary to sufficiently supply $HCO_3^-$. Thus, if carbonic anhydrase is introduced into the plant to which PEPC has been introduced, it is thought that $HCO_3^-$ consumed by the enzyme reaction of PEPC is supplied to cytoplasm, so that the ability of carbon dioxide fixation of the plant can be further promoted.

Carbonic anhydrase genes of dicotyledons such as spinach (Burnell, J. N. et al., Plant Physiol 92:37–40 (1990); Fawcett, T. W. et al., J. Biol. Chem. 265:5414–5417), pea (Roeske, C. A. et al., Nucleic Acid Res. 18:3413 (1990); Majeau, N. et al., Plant Physiol. 95:264–268 (1991)), *Arabidopsis thaliama* (Raines, C. A. et al., Plant Mol. Biol. 20:1143–1148 (1992)) and tobacco (Majeau, N. et al., EMBL Nucleotide Sequence Databases, Accession No. M94135, 1992)) have been isolated and sequenced. However, since the carbonic anhydrases of monocotyledons have enzyme properties different from those of dicotyledons, it is expected that greater effects will be obtained by introducing a carbonic anhydrase gene of a monocotyledon to monocotyledons.

As for carbonic anhydrase genes of monocotyledons, maize carbonic anhydrase gene has been partially sequenced (Keith et al., Plant Physiol. 101:329–332 (1993)). However, the sequenced region is only 210 bp. It is thought that this is too short to encode an active carbonic anhydrase and so cannot be used for genetic manipulation of monocotyledons.

DISCLOSURE OF THE INVENTION

Accordingly, the object of the present invention is to provide a gene encoding a carbonic anhydrase of a monocotyledon.

The present inventors intensively studied to succeed in cloning maize carbonic anhydrase cDNA from maize cDNA library using carbonic anhydrase cDNA of spinach as a probe, and sequencing the cloned gene. The present inventors further succeeded in cloning rice carbonic anhydrase cDNA from rice cDNA library using the thus obtained maize carbonic anhydrase cDNA as a probe, and sequencing the cloned gene, thereby completing the present invention.

That is, the present invention provides a cloned DNA which encodes carbonic anhydrase of a monocotyledon.

The present invention also provides a cloned DNA encoding the amino acid sequence shown in SEQ ID NO. 1, 4, 6 or 8 in Sequence Listing or the same amino acid sequence as shown in SEQ ID NO. 1, 4, 6 or 8 in Sequence Listing except that one or more amino acid is added, deleted or substituted, said amino acid sequence give enzyme activity of carbonic anhydrase.

By the present invention, a cloned DNA which encodes carbonic anhydrase of a monocotyledon was first provided. It is expected that by transforming a monocotyledon with this gene, the ability of carbon dioxide fixation of the plant can be promoted, so that growth of the plant can be accelerated.

BEST MODE FOR CARRYING OUT THE INVENTION

The DNA according to the present invention encodes carbonic anhydrase. Examples thereof include DNAs encoding amino acid sequences of maize carbonic anhydrases, which are shown in SEQ ID NOs. 1, 6 and 8, and the DNA encoding the amino acid sequence of rice carbonic anhydrase, which is shown in SEQ ID NO. 4. The amino acid sequences shown in SEQ ID NOs. 1, 6, 8 and 4 were determined in the examples described below. The nucleotide sequences of the DNAs isolated in the examples described below are shown in SEQ ID NOs. 2, 7, 9 and 5. The amino acid sequences shown in SEQ ID NOs. 2, 7, 9 and 5 are shown in SEQ ID NOs. 1, 6, 8 and 4, respectively. It should be noted that the amino acid sequences shown in SEQ ID NOs. 1, 6, 8 and 4 were also first determined by the present invention.

It is well-known in the art that there are cases wherein the activity of an enzyme is retained even if the amino acid sequence of an enzyme is modified to a small extent, that is, even if one or more amino acids in the amino acid sequence are substituted or deleted, or even if one or more amino acids are added to the amino acid sequence. DNAs encoding the proteins having such modifications and having carbonic anhydrase activity are included within the scope of the present invention. That is, cloned DNAs encoding amino acid sequences having the same amino acid sequence as SEQ ID NO. 1, 4, 6 or 8 except that one or more amino acids are substituted, deleted or added, which give the enzyme activity of carbonic anhydrase, are also included in the scope of the present invention. Similarly, DNAs having the same nucleotide sequence as SEQ ID NO. 2, 5, 7 or 9 except that one or more nucleotides are substituted, deleted or added, which encodes an amino acid sequence giving the enzyme activity of carbonic anhydrase are also included within the scope of the present invention.

Modification of DNA which brings about addition, deletion or substitution of the amino acid sequence encoded thereby can be attained by the site-specific mutagenesis which is well-known in the art (e.g., Nucleic Acid Research, Vol. 10, No. 20, p6487–6500, 1982). In the present specification, "one or more amino acids" means the number of amino acids which can be added, deleted or substituted by the site-specific mutagenesis.

Site-specific mutagenesis may be carried out by, for example, using a synthetic oligonucleotide primer complementary to a single-stranded phage DNA except that the desired mutation as follows. That is, using the above-mentioned synthetic oligonucleotide as a primer, a complementary chain is produced by a phage, and host bacterial cells are transformed with the obtained double-stranded DNA. The culture of the transformed bacterial cells is plated on agar and plaques are formed from a single cell containing the phage. Theoretically, 50% of the new colonies contain the phage having a single-stranded chain carrying the mutation and remaining 50% of the colonies contain the phage having the original sequence. The obtained plaques are then subjected to hybridization with a kinase-treated synthetic probe at a temperature at which the probe is hybridized with the DNA having exactly the same sequence as the DNA having the desired mutation but not with the original DNA sequence that is not completely complementary with the probe. Then the plaques in which the hybridization was observed are picked up, cultured and the DNA is collected.

In addition to the above-mentioned site-specific mutagenesis, the methods for substituting, deleting or adding one or more amino acids without losing the enzyme activity include a method in which the gene is treated with a mutagen and a method in which the gene is selectively cleaved, a selected nucleotide is removed, added or substituted and then the gene is ligated.

The DNAs according to the present invention may be obtained by the methods described in detail in the examples below. Alternatively, since the nucleotide sequences were determined by the present invention, the DNAs according to the present invention can be easily obtained by the PCR method utilizing the genome of maize or rice as a template and also by so called RT-PCR method using their RNAs as a template.

By inserting the DNA according to the present invention into an expression vector for plants by a conventional method and by transforming a monocotyledon with the obtained recombinant vector, carbonic anhydrase can be expressed in the monocotyledon, thereby promoting the ability of carbon dioxide fixation of the plant and, in turn, accelerating the growth of the plant.

The present invention will now be described in more detail by way of examples. It should be noted that the present invention is not restricted to the examples.

EXAMPLE 1
Isolation of Maize Carbonic Anhydrase cDNA

From green leaves of maize, RNAs were extracted and polyA$^+$RNAs were isolated using DYNABEADS (commercially available from BERITUS) according to the instructions by the manufacturer. According to a conventional method, phage-infected bacterial cells were plated on a medium and plaques obtained by culturing the plate at 37° C. were transferred to a nylon membrane (Hybond N$^+$, commercially available from AMERSHAM). The library was screened by using a probe obtained by labelling the EcoRI fragment (790 bp) of spinach carbonic anhydrase cDNA (Burnell et al., (1990) Plant Physiol. 92:37–40) with [α-$^{32}$P]dCTP (commercially available from AMERSHAM) by using Gigaprime Labelling kit (commercially available from Bresatec, Adelaide, Australia), and positive clones were selected. Hybridization was performed at 42° C. for 16–24 hours in a solution containing 6×SSPE, 5×Denhalt's solution, 0.5% (w/v) SDS, 100 μg/ml of herring sperm DNA, 10 mM phosphate buffer (pH 7.0) and 50% (v/v) formamide, to which the probe labelled with $^{32}$P was added. The membranes were then washed in 2×SSC containing 0.1% (w/v) SDS at room temperature for 30 minutes and then with 1×SSC containing 0.1% (w/v) SDS at 60° C. for 30 minutes. The membranes were then subjected to autoradiography and positive clones were selected. The inserts of the obtained clones were subcloned into pTZ18R and sequenced by dideoxy method. The determined sequence is shown in SEQ ID. NO. 2. This sequence has a homology of 60.3% with the EcoRI fragment of the spinach carbonic anhydrase used as a probe, and has a homology of 98.8% with the reported maize cDNA fragment having a homology with the gene encoding pea chloroplast type carbonic anhydrase.

EXAMPLE 2
Isolation of Rice Carbonic Anhydrase cDNA
(1) Purification of Rice Carbonic Anhydrase and Determination of Amino Acid Sequence of N-terminal One hundred grams of rice leaves cultivated under long day regimen was ground with 300 ml of extraction buffer (50 mM Hepes-KOH pH 7.5, 10 mM MgSO$_4$, 1 mM EDTA, 20 mM 2-mercaptoethanol). The resultant was filtered through two layers of MIRACLOTH (commercially available from KARBIOCHEM), and the filtrate was centrifuged at 30,000×g for 20 minutes to remove insoluble materials, thereby obtaining a crude extract. The crude extract was fractioned by sodium sulfate of 40–60% saturation (0° C.). The obtained precipitate was dissolved in a column buffer (20 mM Hepes-KOH pH 7.5, 20 mM 2-mercaptoethanol) and applied to preliminarily equilibrated Sephadex G25 (commercially available from Pharmacia) column (inner diameter 2.5 cm×35 cm), thereby carrying out desalination. The desalinated crude extract was applied to preliminarily equilibrated DEAE-Cellulose 52 (commercially available from WHATMAN) column (inner diameter 2.5 cm×20 cm). After sufficiently washing the column with the column buffer, the adsorbed proteins were eluted by linear gradient of KCl from 0 to 0.3M. The fractions exhibiting carbonic anhydrase activity were combined and solid ammonium sulfate was added to a concentration of 65% (0° C.) to precipitate the proteins. The generated precipitate was dissolved in 3 ml of column buffer and the solution was applied to Sepharose CL-6B (commercially available from Pharmacia) column (inner diameter 2.5 cm×96 cm) preliminarily equilibrated with the column buffer, thereby fractioning the proteins. Among the eluted fractions, the fraction exhibiting the highest carbonic anhydrase activity was subjected to SDS-polyacrylamide gel electrophoresis and the band of carbonic anhydrase protein was identified by Western blotting using anti-maize carbonic anhydrase polyclonal antibody. On the other hand, the isolated protein after the SDS-polyacrylamide gel electrophoresis was electrically transferred to a PVDF membrane (commercially available from Millipore), and the band of carbonic anhydrase was cut out. The amino acid sequence of N-terminal region of the protein was determined by gas phase Edman degradation method using 447A Protein Sequencer commercially available from Applied Biosystems. The determined amino acid sequence is shown in SEQ ID. NO. 3.

(2) Isolation of Rice Carbonic Anhydrase cDNA

From green leaves of maize, RNAs were extracted and polyA$^{30}$RNAs were isolated using DYNABEADS (commercially available from BERITUS) according to the instructions by the manufacturer. A cDNA library employing as a vector a phage vector called λZapII vector using cDNA synthesis kit and direct cloning kit which are commercially available from Pharmacia. The library was screened by using a probe obtained by labelling the maize carbonic anhydrase cDNA fragment (1.8 kb) with [α-$^{32}$P]dCTP (commercially available from AMERSHAM) by using Gigaprime Labelling kit (commercially available from Bresatec, Adelaide, Australia), and positive clones were selected. Hybridization was performed at 42° C. for 16–24 hours in a solution containing 6×SSPE, 5×Denhalt's solution, 0.5% (w/v) SDS, 100 μg/ml herring sperm DNA, 10 mM phosphate buffer (pH 7.0) and 50% (v/v) formamide, to which the probe labelled with $^{32}$P was added. The membrane was then washed in 2×SSC containing 0.1% (w/v) SDS at room temperature for 30 minutes and then with 1×SSC containing 0.1% (w/v) SDS at 60° C. for 30 minutes. The membrane was then subjected to autoradiography and positive clones were selected. The obtained clones were subcloned into a vector pBluescript by in vivo excision method and then sequenced by dideoxy method using T7 Sequence kit (commercially available from Pharmacia) (SEQ ID. NO. 5). In the amino acid sequence deduced from this nucleotide sequence, a region identical to the amino acid sequence of the N-terminal region determined in (1) existed. Therefore, the obtained cDNA clone was judged to be a gene encoding carbonic anhydrase.

EXAMPLE 3

Isolation of Maize Carbonic Anhydrase cDNA

The same procedure as in Example 1 was repeated except that 5'-end region (EcoRI-BstXI fragment, 135 bp) of the maize carbonic anhydrase cDNA obtained in Example 1 was used as the probe in place of spinach carbonic anhydrase cDNA. As a result, two carbonic anhydrase cDNA clones (CAI and CAII) were obtained. Although these cDNAs have very high homologies with the maize carbonic anhydrase cDNA obtained above, they are not completely identical. The nucleotide sequences of CAI and CAII as well as deduced amino acid sequences are shown in SEQ ID NOs. 7 and 9, respectively.

INDUSTRIAL AVAILABILITY

Since the DNAs according to the present invention encode carbonic anhydrase of monocotyledons, it is expected that by transforming a monocotyledons with the DNA, the ability of carbon dioxide fixation of the plant may be promoted and growth of the plant may be accelerated.

We claim:

1. An isolated and purified DNA encoding the amino acid sequence according to SEQ ID NO. 1.

2. An isolated and purified DNA sequence having the nucleotide sequence according to SEQ ID NO. 2.

3. An isolated and purified DNA encoding the amino acid sequence according to SEQ ID NO. 4.

4. An isolated and purified DNA sequence having the nucleotide sequence according to SEQ ID NO. 5.

5. An isolated and purified DNA encoding the amino acid sequence according to SEQ ID NO. 6.

6. An isolated and purified DNA sequence having the nucleotide sequence according to SEQ ID NO. 7.

7. An isolated and purified DNA encoding the amino acid sequence according to SEQ ID NO. 8.

8. An isolated and purified DNA sequence having the nucleotide sequence according to SEQ ID NO. 9.

* * * * *